(12) United States Patent
Jaeger

(10) Patent No.: US 9,244,033 B2
(45) Date of Patent: Jan. 26, 2016

(54) METHOD FOR ONLINE DETECTION OF LINER BUCKLING IN A STORAGE SYSTEM FOR PRESSURIZED GAS

(71) Applicant: GM Global Technology Operations LLC, Detroit, MI (US)

(72) Inventor: Ralf Jaeger, Worms (DE)

(73) Assignee: GM Global Technology Operations LLC, Detroit, MI (US)

( * ) Notice: Subject to any disclaimer, the term of this patent is extended or adjusted under 35 U.S.C. 154(b) by 182 days.

(21) Appl. No.: 13/749,195

(22) Filed: Jan. 24, 2013

(65) Prior Publication Data

US 2014/0203026 A1      Jul. 24, 2014

(51) Int. Cl.

| F17C 1/02 | (2006.01) |
|---|---|
| G01N 27/24 | (2006.01) |
| F17C 1/00 | (2006.01) |
| F17C 13/00 | (2006.01) |
| F17C 13/02 | (2006.01) |

(52) U.S. Cl.
CPC *G01N 27/24* (2013.01); *F17C 1/00* (2013.01); *F17C 13/002* (2013.01); *F17C 13/02* (2013.01); *F17C 2201/0109* (2013.01); *F17C 2201/056* (2013.01); *F17C 2203/0604* (2013.01); *F17C 2203/0624* (2013.01); *F17C 2203/0636* (2013.01); *F17C 2203/0643* (2013.01); *F17C 2203/0646* (2013.01); *F17C 2203/0663* (2013.01); *F17C 2221/011* (2013.01); *F17C 2221/012* (2013.01); *F17C 2221/031* (2013.01); *F17C 2223/0123* (2013.01); *F17C 2223/036* (2013.01); *F17C 2250/036* (2013.01); *F17C 2250/0404* (2013.01); *F17C 2250/0478* (2013.01); *F17C 2250/0491* (2013.01); *F17C 2250/0495* (2013.01); *F17C 2260/015* (2013.01); *F17C 2270/0168* (2013.01); *F17C 2270/0184* (2013.01); *Y02E 60/321* (2013.01)

(58) Field of Classification Search
CPC ............ F17C 1/00; F17C 13/02; G01N 27/24
USPC .......... 220/581, 588, 589, 530, 586; 324/661, 324/671, 658, 662, 663
See application file for complete search history.

(56) References Cited

U.S. PATENT DOCUMENTS

| 3,757,982 | A | * | 9/1973 | Isenberg et al. | ........... 220/560.15 |
|---|---|---|---|---|---|
| 4,026,276 | A | * | 5/1977 | Chubbuck | ..................... 600/407 |
| 6,640,641 | B1 | * | 11/2003 | Benestad | ......................... 73/718 |
| 6,708,502 | B1 | * | 3/2004 | Aceves et al. | ................... 62/45.1 |
| 8,550,286 | B2 | * | 10/2013 | Lukiyanets et al. | .......... 220/589 |
| 2006/0152380 | A1 | * | 7/2006 | Anderson et al. | .............. 340/679 |
| 2008/0035647 | A1 | * | 2/2008 | Fuller | ............................ 220/530 |
| 2008/0179333 | A1 | * | 7/2008 | Fuller et al. | .................... 220/530 |
| 2009/0283176 | A1 | * | 11/2009 | Berry et al. | ....................... 141/1 |
| 2011/0139796 | A1 | * | 6/2011 | Lukiyanets et al. | .......... 220/581 |
| 2013/0248524 | A1 | * | 9/2013 | Goad | ........................... 220/4.13 |

\* cited by examiner

*Primary Examiner* — Lisa Caputo
*Assistant Examiner* — Jonathan Dunlap
(74) *Attorney, Agent, or Firm* — Brooks Kushman P.C.

(57) ABSTRACT

A pressurized gas storage system includes an outer shell having an inner and outer surface. The inner surface defines an inner volume for holding a pressurized gas. A first electrically conductive layer is attached to the outer shell. An inner liner is disposed over the inner surface. A second electrically conductive layer is attached to the inner liner. A capacitance meter measures the capacitance between the first and second electrically conductive layers wherein a change in capacitance indicates buckling in the storage system.

6 Claims, 4 Drawing Sheets

METHOD FOR ONLINE DETECTION OF LINER BUCKLING IN A STORAGE SYSTEM FOR PRESSURIZED GAS

TECHNICAL FIELD

The present invention relates to gas storage systems for fuel cell operated vehicles that detect liner buckling.

BACKGROUND

Fuel cells are used as an electrical power source in many applications. In particular, fuel cells are proposed for use in automobiles to replace internal combustion engines. A commonly used fuel cell design uses a solid polymer electrolyte ("SPE") membrane or proton exchange membrane ("PEM") to provide ion transport between the anode and cathode. In proton exchange membrane type fuel cells, hydrogen is supplied to the anode as fuel and oxygen is supplied to the cathode as the oxidant. The oxygen can either be in pure form ($O_2$) or air (a mixture of $O_2$ and $N_2$). PEM fuel cells typically have a membrane electrode assembly ("MEA") in which a solid polymer membrane has an anode catalyst on one face, and a cathode catalyst on the opposite face.

Modern fuel cell vehicles store hydrogen in pressure vessels with pressures up to 700 bar. Typically, these vessels are made of a liner material that functions as a barrier to gas diffusion. The liner is typically surrounded by a matrix of carbon fiber layers which are mainly responsible to hold the stress of a 700 bar filled vessel. In some cases, the liner which is a very soft material, delaminates from the fiber compound and buckles to the inside. It is believed that such delamination occurs at around a pressure of zero bar inside the vessel (i.e., an empty vessel). It is also observed that buckling can also occur at higher inner pressures when the delta pressure to the outside is high enough. This is the case when gas diffusing through the liner material is trapped between the compound and the liner. Liner buckling is regarded as a contributor to high stress inside the liner material which then could lead to durability issues and fatigue cracks of the liner material.

Accordingly, there is a need for improved systems for storing pressurized gases for fuel cell applications that provide an online detection method to detect the start of a liner buckling.

SUMMARY

The present invention solves one or more problems of the prior art by providing, in at least one embodiment, a storage system for pressurized gas. The pressurized gas storage system includes an outer shell having an inner and outer surface. The inner surface defines an inner volume for holding a pressurized gas. A first electrically conductive layer is attached to the outer shell. An inner liner is disposed over the inner surface. A second electrically conductive layer is attached to the inner liner. Characteristically, the second electrical layer is electrically insulated from the first electrically conductive layer. A capacitance meter measures the capacitance between the first and second electrically conductive layers wherein a change in capacitance indicates buckling in the storage system.

In another embodiment, a storage system for pressurized gas is provided. The pressurized gas storage system includes an outer shell having an inner and outer surface. The inner surface defines an inner volume for holding a pressurized gas. Characteristically, the outer shell includes an electrically conductive composite. An inner liner is disposed over the inner surface. An electrically conductive layer is attached to the inner liner. The electrically conductive layer is electrically insulated from the outer shell. A capacitance meter measures the capacitance between the outer shell and the electrically conductive layer wherein a change in capacitance indicates buckling in the storage system.

In another embodiment, a method of determining buckling in a pressurized gas storage system is provided. The method includes steps of providing an outer shell having an inner and outer surface, providing a first electrically conductive layer attached to the outer shell, providing an inner liner disposed over the inner surface and a second electrically conductive layer; providing a second electrically conductive layer associated with the inner liner, and providing a capacitance meter that measures the capacitance between the first electrically conductive layer and the second electrically conductive layer. The inner surface defines an inner volume for holding a pressurized gas. Characteristically, the second electrical layer is electrically insulated from the first electrically conductive layer. The capacitance between the first electrically conductive layer and the second electrically conductive layer is measured such that a change in capacitance indicates buckling in the storage system.

Advantageously, the system and method of the invention are used to detect liner buckling so that the pressure is controlled to stop the buckling or to count the number of buckling events to correlate to material tests.

BRIEF DESCRIPTION OF THE DRAWINGS

Exemplary embodiments of the present invention will become more fully understood from the detailed description and the accompanying drawings, wherein.

DETAILED DESCRIPTION

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Figure 1:
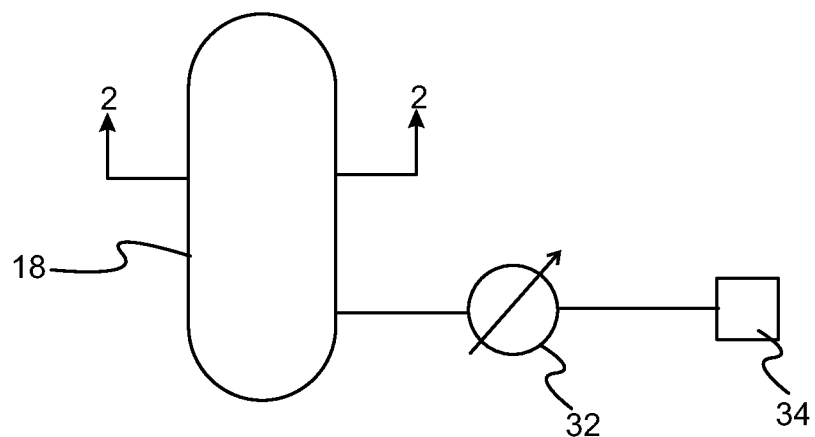
FIG. 1 is a schematic illustration of a pressurized gas storage system having a buckling detection mechanism.
Figure 2:
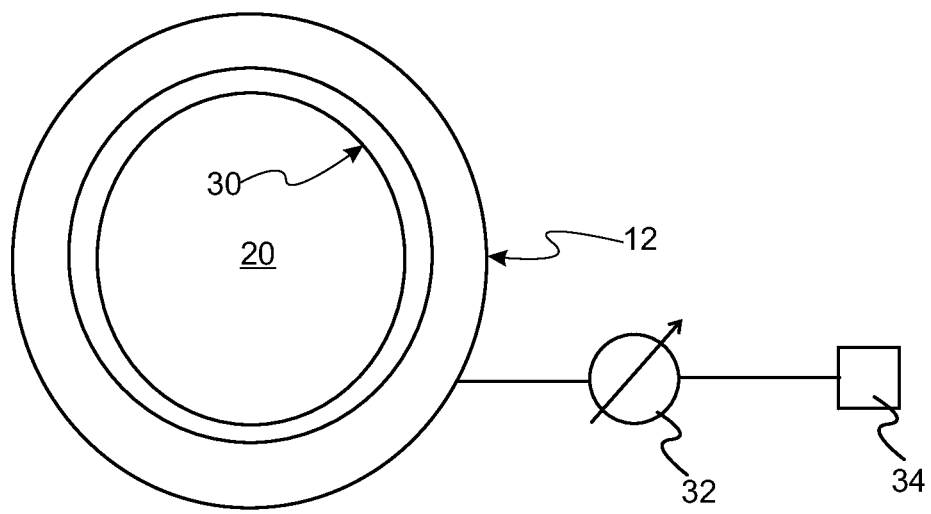
FIG. 2 is a schematic cross section of a pressurized gas storage system having a buckling detection mechanism.
Figure 3:
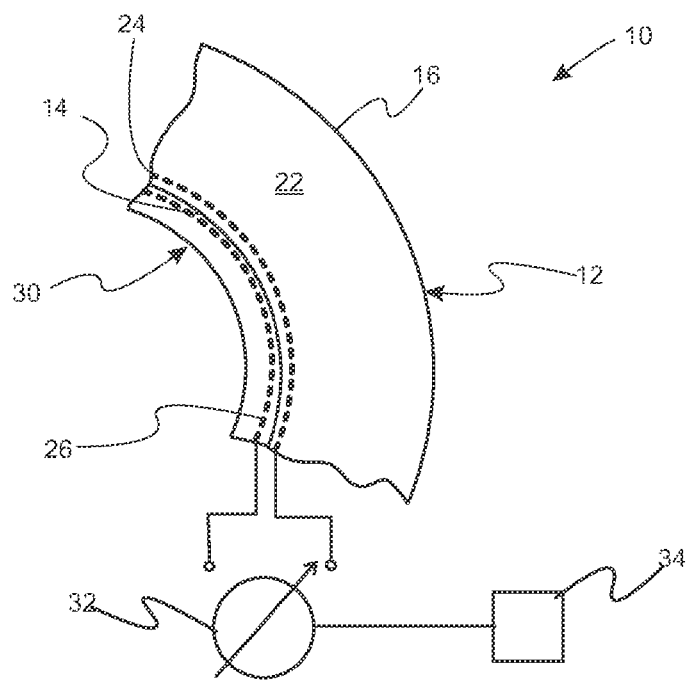
FIG. 3 is a schematic cross section of a section of a pressurized gas storage system having a buckling detection mechanism.

With reference to FIGS. 1, 2, and 3, schematics illustrating a pressurized gas storage system are provided. Pressurized gas storage system 10 includes outer shell 12 having an inner surface 14 and outer surface 16. Inner surface 14 defines inner volume 20 for holding a pressurized gas. First electrically conductive layer 24 is attached to outer shell 12. Outer shell 12 defines vessel 18 for holding a pressurized gas such as hydrogen or an oxidizing gas (e.g., oxygen, air, etc.) to be used to power a fuel cell. In a refinement, vessel 18 has a circular cross section. Typically, the pressurized gas may be stored at a pressure from about 100 bar to 700 bar. Inner liner 30 is disposed over inner surface 14. Second electrically conductive layer 26 is attached to inner liner 30. Capacitance meter 32 measures the capacitance between the first electrically conductive layer 24 and second electrically conductive layer 26 wherein a change in capacitance indicates buckling in storage system 10. Measured change in capacitance indicates buckling of inner liner 30. In a refinement, gas storage system 10 further includes an indicator 34 to indicate buckling of the liner. Advantageously, the indicator provides a warning or alarm when buckling is detected.

As set forth above, first electrically conductive layer 24 is attached to outer shell 12. In a variation, first electrically conductive layer 24 is embedded in outer shell 12. In a refinement, first electrically conductive layer 24 may be a metal foil or a metal grid. Suitable metals include but are not limited to, aluminum, stainless steels, titanium and the like. In another refinement, outer shell 16 includes a solid matrix 22 such as a composite. Examples of suitable composites include but are not limited to, carbon composites which include carbon fibers or powder dispersed in a resin. It should be appreciated that the volume of the vessel formed from outer shell 12 enlarges when pressurized. Therefore, first electrically conductive layer 24 must be flexible enough to expand and contract with the vessel. For example, the change in volume is calibrated in order to properly detect buckling. In a refinement, the capacitance versus pressure is determined for the vessel.

Figure 4:
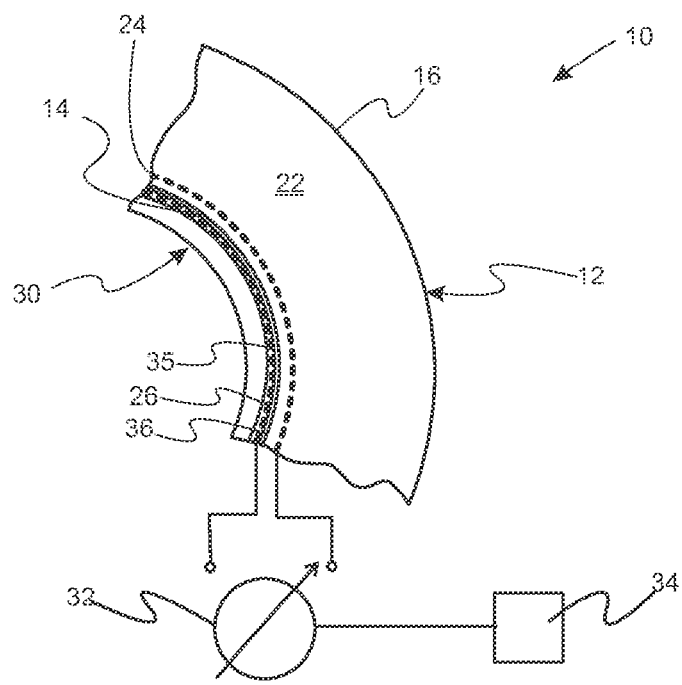
FIG. 4 is a schematic cross section of a section of a pressurized gas storage system having a buckling detection mechanism with an insulating layer between the first electrically conductive layer and the second electrically conductive layer.

As set forth above, second electrically conductive layer 26 is attached to inner liner 30. In one variation, second electrically conductive layer 26 is embedded in inner liner 30. In another variation as set forth in FIG. 4, second electrically conductive layer 26 is attached to surface 35 of inner liner 30. In this variation, electrically insulating layer (e.g., a dielectric layer) 36 is interposed between second electrically conductive layer 26 and outer shell 12. In either of these variations, second electrically conductive layer 26 may be a metal foil or a metal grid. Suitable metals include, but are not limited to, aluminum, stainless steels, titanium and the like.

In combination, first electrically conductive layer 24 and second electrically conductive layer 26 with dielectric interposed form a capacitor. Therefore, it is necessary that the first electrically conductive layer 24 stays with the outer shell 12 and that the second electrically conductive layer 26 stays with inner liner 30 during buckling.

Figure 5:
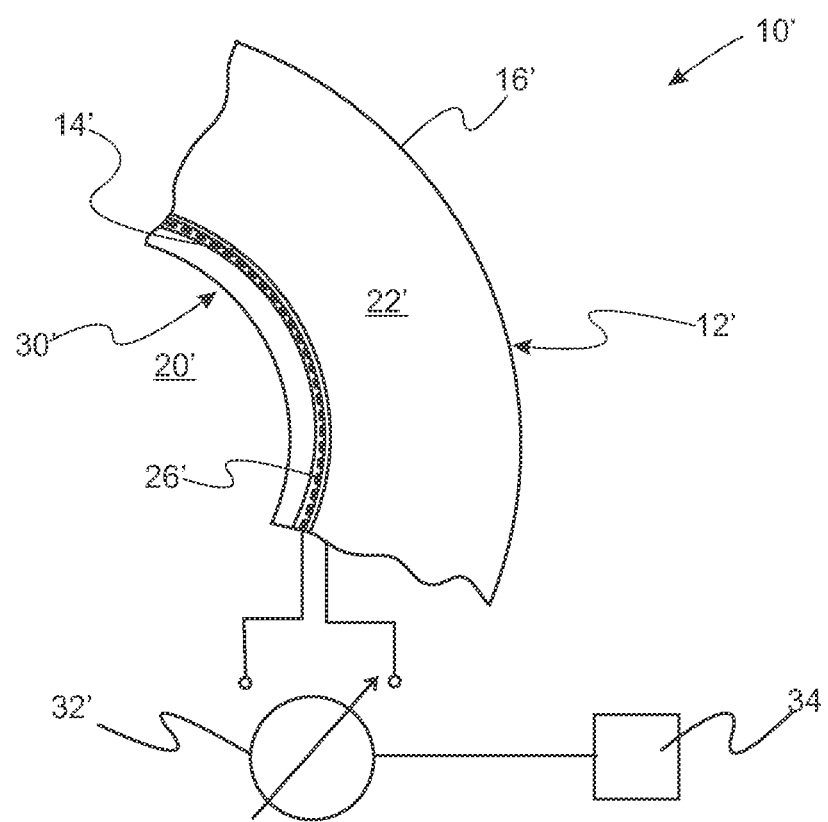
FIG. 5 is a schematic cross section illustrating the buckling of the inner liner that is detected by the systems set forth in FIGS. 1-4.

With reference to FIG. 5, a variation in which the outer shell is formed from an electrically conductive material is provided. In this variation, the first electrically conductive layer is not needed. For example, outer shell 12' is formed of a carbon composite that includes carbon fiber or carbon powder dispersed in a resin. In particular, pressurized gas storage system 10' includes outer shell 12' having an inner surface 14' and outer surface 16' Inner surface 14' defines inner volume 20' for holding a pressurized gas. Outer shell 12' defines a vessel for holding a pressurized gas such as hydrogen or an oxidizing gas (e.g., oxygen, air, etc.) to be used to power a fuel cell as set forth above. Inner liner 30' is disposed over inner surface 14'. Electrically conductive layer 26' is attached to inner liner 30'. Capacitance meter 32' measures the capacitance between outer shell 12' and electrically conductive layer 26' wherein a change in capacitance indicates buckling in storage system 10'. Measured change in capacitance indicates buckling of inner liner 30'. In a refinement, gas storage system 10' further includes an indicator 34 to indicate buckling of the liner. In a variation, an electrically insulating layer is interposed between electrically conductive layer 26' and outer shell 12' as set forth above in connection with the description of FIG. 4.

Figure 6:
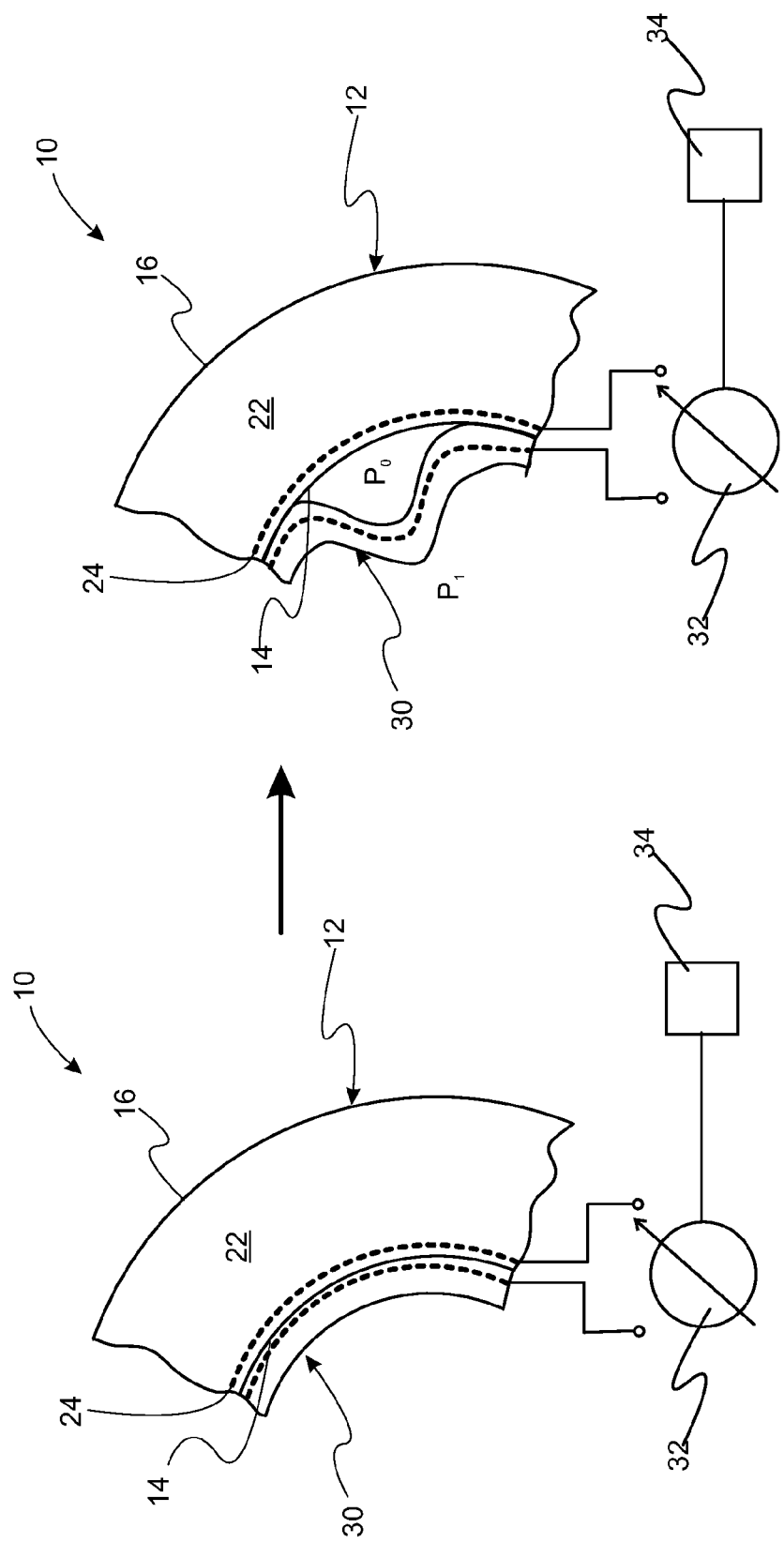
FIG. 6 is a schematic illustrating the buckling of the inner liner that is detected by the systems set forth above.

With reference to FIG. 6, a schematic illustrating the buckling of the inner liner that is detected by the systems set forth above is provided. Inner liner 30 separates from outer shell 12 with pressure $P_0$ in space 50 formed at the separation being greater than the pressure $P_1$ on the inside of inner liner 30. This separation is detected as a change in capacities between first electrically conductive layer 24 and second electrically conductive layer 26. Alternatively for the design of FIG. 5, this separation is detected as a change in capacities between electrically conductive outer shell 12 and electrically conductive layer 26'.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for detection of liner buckling in a storage system for pressurized gas, the method comprising:
- providing an outer shell having an inner surface and outer surface, the outer shell including a solid matrix, the inner surface defining an inner volume holding pressurized gas at a pressure 100 bar to 700 bar;
- providing a first electrically conductive layer attached to the outer shell;
- providing an inner liner disposed over the inner surface;
- providing a second electrically conductive layer associated with the inner liner, the second electrically conductive layer being electrically insulated from the first electrically conductive layer; and
- providing a capacitance meter that measures capacitance between the first electrically conductive layer and the second electrically conductive layer; and
- detecting buckling in the storage system in which the inner liner separates from the outer shell to form a separation, the buckling being detected from the capacitance between the first electrically conductive layer and the second electrically conductive layer.

2. The method of claim 1 wherein the solid matrix comprises a carbon fiber composite.

3. The method of claim 1 wherein the first electrically conductive layer is embedded in the solid matrix.

4. The method of claim 1 wherein the first electrically conductive layer is positioned at the inner surface.

5. The method of claim 1 wherein the second electrically conductive layer is embedded in the inner liner.

6. The method of claim 1 wherein the outer shell has a circular cross section.

* * * * *